(12) United States Patent
Ashton et al.

(10) Patent No.: US 7,572,248 B2
(45) Date of Patent: Aug. 11, 2009

(54) UNITARY DISPOSABLE PANT-TYPE GARMENT WITH NON-ELASTICIZED GAP BETWEEN STRETCH SIDE PANELS AND ABSORBENT ASSEMBLY

(75) Inventors: Gregory Ashton, Symmes Township, OH (US); Michael Charles Raufman, Liberty Township, OH (US); Joseph Hung Lam, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 262 days.

(21) Appl. No.: 10/434,378

(22) Filed: May 8, 2003

(65) Prior Publication Data

US 2004/0225273 A1  Nov. 11, 2004

(51) Int. Cl.
*A61F 13/15* (2006.01)
*A61F 13/20* (2006.01)

(52) U.S. Cl. .................. 604/385.01; 604/385.04; 604/378

(58) Field of Classification Search ............ 604/385.28, 604/385.25, 385.26, 385.27, 385.01, 385.101, 604/385.22–385.24, 385.21, 358
See application file for complete search history.

(56) References Cited

U.S. PATENT DOCUMENTS

| | | |
|---|---|---|
| 2,075,189 A | 3/1937 | Galligan et al. |
| 3,025,199 A | 3/1962 | Harwood |
| 3,848,594 A | 11/1974 | Buell |
| 3,860,003 A | 1/1975 | Buell |
| 3,911,173 A | 10/1975 | Sprague, Jr. |
| 3,929,135 A | 12/1975 | Thompson |
| 4,107,364 A | 8/1978 | Sisson |
| 4,209,563 A | 6/1980 | Sisson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,699,622 A | 10/1987 | Toussant et al. |
| 4,704,115 A | 11/1987 | Buell |
| 4,738,677 A * | 4/1988 | Foreman ............... 604/385.27 |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,909,803 A | 3/1990 | Aziz et al. |
| 4,938,753 A * | 7/1990 | Van Gompel et al. .. 604/385.29 |

(Continued)

FOREIGN PATENT DOCUMENTS

EP  0 797 968 A1  10/1997

*Primary Examiner*—Michele Kidwell
(74) *Attorney, Agent, or Firm*—Charles R. Matson; Matthew P. Fitzpatrick (57) ABSTRACT

The present invention relates to disposable pant-type garments. Examples of such disposable pant-type garments include disposable underwear, adult incontinence products, disposable pull-on diapers and training pants, and disposable panties for menstrual use.

11 Claims, 6 Drawing Sheets

U.S. PATENT DOCUMENTS

| | | |
|---|---|---|
| 4,946,527 A | 8/1990 | Battrell |
| 4,963,140 A | 10/1990 | Robertson et al. |
| 4,988,344 A | 1/1991 | Reising et al. |
| 4,988,345 A | 1/1991 | Reising et al. |
| 5,006,394 A | 4/1991 | Baird |
| 5,026,364 A | 6/1991 | Robertson |
| 5,037,416 A | 8/1991 | Allen et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,190,563 A | 3/1993 | Herron et al. |
| 5,196,000 A * | 3/1993 | Clear et al. ............ 604/385.29 |
| 5,221,274 A | 6/1993 | Buell et al. |
| 5,234,423 A | 8/1993 | Alemany et al. |
| 5,260,345 A | 11/1993 | DesMarais et al. |
| 5,269,775 A | 12/1993 | Freeland et al. |
| 5,330,458 A | 7/1994 | Buell et al. |
| 5,342,338 A | 8/1994 | Roe |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,649,918 A * | 7/1997 | Schleinz ................ 604/385.26 |
| 5,669,897 A | 9/1997 | Lavon et al. |
| 5,865,823 A | 2/1999 | Curro |
| 5,899,895 A * | 5/1999 | Robles et al. .......... 604/385.29 |
| 5,906,603 A * | 5/1999 | Roe et al. .............. 604/385.24 |
| 5,938,648 A | 8/1999 | LaVon et al. |
| 5,968,025 A | 10/1999 | Roe et al. |
| 6,004,306 A | 12/1999 | Robles et al. |
| 6,050,985 A * | 4/2000 | Lavon et al. ........... 604/385.21 |
| 6,443,940 B1 | 9/2002 | Ashton et al. |
| 2001/0007936 A1* | 7/2001 | Shimoe et al. ......... 604/385.24 |
| 2002/0087139 A1* | 7/2002 | Popp et al. ............. 604/385.24 |

* cited by examiner

UNITARY DISPOSABLE PANT-TYPE GARMENT WITH NON-ELASTICIZED GAP BETWEEN STRETCH SIDE PANELS AND ABSORBENT ASSEMBLY

CROSS REFERENCE TO RELATED APPLICATIONS

Not applicable.

FIELD OF INVENTION

The present invention relates to disposable pant-type garments. Examples of such disposable pant-type garments include disposable underwear, adult incontinence products, disposable pull-on diapers and training pants, and disposable panties for menstrual use.

BACKGROUND OF THE INVENTION

Infants and other incontinent individuals wear disposable garments such as diapers to receive and contain urine and other body exudates. Disposable pull-on garments having fixed sides, which are also called "pant type" garments, have become popular for use on children able to walk and often who are toilet training. These pull-on garments have side panels with edges that are seamed together to form two leg openings and a waist opening. In order to contain body exudates as well as fit a wide variety of body shapes and sizes these pull-on garments need to fit snugly about the waist and legs of the wearer without drooping, sagging or sliding down from the pull-on garments position on the torso.

To prevent pull-on garments from drooping, sagging or sliding down from the torso of a wearer, it is believed that proper forces should be generated at the waist and side panel areas of pull-on garments and applied to the torso of wearer. For example, some prior art discloses the use of a plurality of elastic members which have different expanding stresses to provide controlled fitness forces to body. Since these pull-on garments need to use and handle the plurality of elastic members, their manufacturing processes tend to become complicated to handle the elastic members. Furthermore, it is also desired to use the minimum amount of elastic material necessary, while still preventing drooping, sagging or sliding of the pull-on garment. Any savings made in the amount of elastic material used, even savings of a fraction of a cent, are significant. Pull-on garments, such as adult incontinence products, disposable pull-on diapers training pants, disposable panties and the like, are high volume consumables and any cost savings per pull-on garment, no matter how small, translates into significant savings when considering, for example, an entire production run of pull-on garments.

However, the process of preventing pull-on garments from drooping, sagging or sliding down as well as minimizing the amount of elastic material used can result in a garment which has an appearance and a feel to the wearer of a disposable diaper and less like conventional undergarments. Most of the underwear in the market has a finished edge without uncontrolled flaps or panels. Thus, consumers perceive that it is ideal for pull-on garments to have a homogeneous cloth-like outer cover without an uncontrolled edge to enhance the underwear-like aesthetic of the garment. This appearance has a significant negative impact for pull-on garments, both for those intended for infant and adult use. In the case of a child, especially those toilet training, the appearance of a pull-on garments can have a significant impact on the child's desire to use the product. All the energy, time and effort invested by a caregiver in the toilet training process encouraging the child that they are a "big boy" or "big girl" can be for naught if the pull-on garments used in the process appear to be a regular diaper instead of undergarments, which is the aim of the toilet training process. Likewise few adults would be comfortable wearing pull-on garments which look and feel like a child's diaper.

Thus, the need remains for a pull-on garment which does not droop, sag or slide down the torso of wearer while being worn, and has the appearance and feel of conventional undergarments.

SUMMARY OF THE INVENTION

A first aspect of the present invention provides a unitary disposable pant-like absorbent article for containing bodily wastes from a wearer. The article comprises:
  (a) a chassis comprising an outer cover defining a pant-like garment having two leg openings and a waist opening, the chassis comprising a wearer-facing surface, and a pair of opposing side regions, each of the pair of opposing side regions comprising at least one stretchable member disposed on the wearer-facing surface, each of the stretchable members having a pair of longitudinally oriented side edges;
  (b) an absorbent assembly, the absorbent assembly comprising a liquid pervious topsheet, a liquid impervious backsheet associated with the topsheet and an absorbent core disposed between the topsheet and the backsheet, the absorbent assembly being joined to the wearer-facing surface of the chassis, the absorbent assembly having a pair of longitudinally oriented side edges, wherein the absorbent assembly's pair of longitudinally oriented side edges are in a spaced apart relationship with each of the stretchable member's pair of longitudinally oriented side edges defining a front longitudinally orientated non-elasticized portion and a rear longitudinally orientated non-elasticized portion therebetween; and
  (c) at least one barrier cuff, the barrier cuff being attached to one of the longitudinally oriented side edges of the absorbent assembly.

A second aspect of the present invention provides a unitary disposable pant-like absorbent article for containing bodily wastes from a wearer. The article comprises:
  (a) a chassis comprising an outer cover defining a pant-like garment having two leg openings, a waist opening, and a wearer-facing surface, the chassis comprising:
    (i) a first side region, the first side region comprising a first stretchable member, the first stretchable member being disposed on the wearer-facing surface of the chassis;
    (ii) a second side region, the second side region comprising a second stretchable member, the second stretchable member being disposed on the wearer-facing surface of the chassis;
  (b) an absorbent assembly, the absorbent assembly having a first longitudinal side edge and a second longitudinal side edge, the absorbent assembly comprising a liquid pervious topsheet, a liquid impervious backsheet associated with the topsheet and an absorbent core disposed between the topsheet and the backsheet, the absorbent assembly being joined to the wearer-facing surface of the chassis such that the first and second longitudinal side edges are in a spaced apart relationship with each of the first and second stretchable members defining a front longitudinally orientated non-elasticized portion and a rear longitudinally orientated non-elasticized portion therebetween;

(c) a first barrier cuff, the first barrier cuff being attached to the first longitudinal side edge of the absorbent assembly; and (d) a second barrier cuff, the second barrier cuff being attached to the second longitudinal side edge of the absorbent assembly.

It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

All documents cited are, in relevant part, incorporated herein by reference; the citation of any document is not to be construed as an admission that it is prior art with respect to the present invention. All percentages, ratios and proportions are by weight, and all temperatures are in degrees Celsius (° C.), unless otherwise specified. All measurements are in SI units unless otherwise specified.

BRIEF DESCRIPTION OF THE DRAWINGS

The above-mentioned and other features and objects of this invention and the manner of attaining them will become more apparent, and the invention itself will be better understood, by reference to the following description of the invention taken in conjunction with the accompanying drawings, wherein.

DETAILED DESCRIPTION OF THE INVENTION

Herein, "pant-like" refers to articles of wear which have a defined waist opening and a pair of leg openings and which are pulled onto the body of the wearer by inserting the legs into the leg openings and pulling the article up over the waist. These articles of wear may also be referred to as "pull-on" or "pull-on garments". Herein, "disposable" describes articles which are not intended to be laundered or otherwise restored or reused as a garment (i.e., they are intended to be discarded after a single use and, preferably, to be recycled, composted or otherwise disposed of in an environmentally compatible manner). A "unitary" disposable pant-like absorbent article refers to pull-on garments which are formed of separate parts united together to form a coordinated entity, but the pair of opposing side regions are not separate elements joined to a separate chassis; rather, the pair of opposing side regions are formed by at least one layer which also forms the chassis of the garment (i.e., the garment does not require separately manipulative panels such as a separate chassis and separate pair of opposing side regions). The pull-on garment is also preferably "absorbent" to absorb and contain the various exudates discharged from the body. Herein, "pull-on diaper" refers to pant-like articles generally worn by infants and other incontinent individuals to absorb and contain urine and feces. It should be understood, however, that the present invention is also applicable to other pant-like articles such as training pants, incontinent briefs, feminine hygiene garments or panties, and the like. Herein "chassis" is the foundational element upon which the remainder of the article is built-up or overlaid. Herein, "uncontracted state" is used herein to describe states of pull-on garments in its unseamed (i.e., seams are removed), flat and relaxed condition wherein all elastic materials used are removed. Herein, "stretchable" refers to materials that are capable of extending in at least one direction to a certain degree without undue rupture. Herein, "elasticity", "elastomeric" and "elastically stretchable" refer to stretchable materials that have the ability to return to approximately their original dimensions after the force that extended the material is removed. Herein, any material or element described as "stretchable" may also be elastically stretchable unless otherwise provided.

Figure 1:
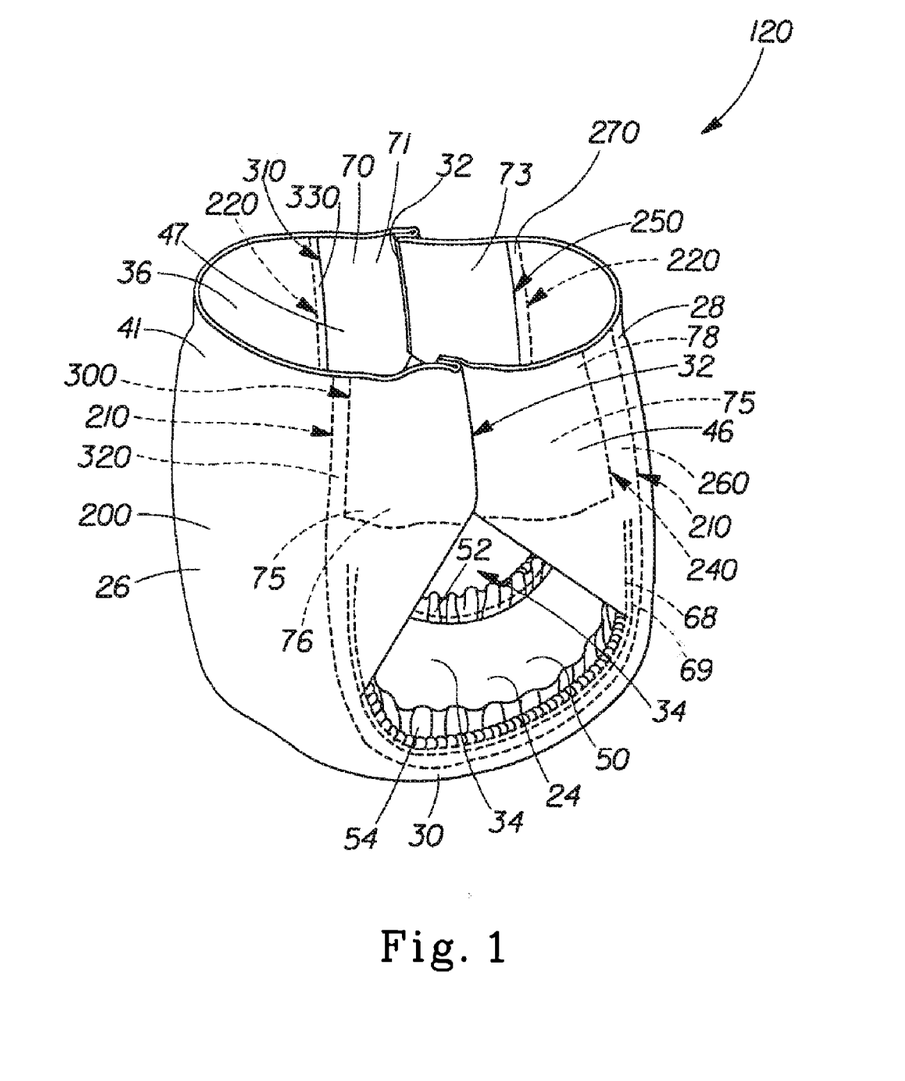
FIG. 1 is a perspective view of one embodiment of the disposable pant-type garment of the present invention.
Figure 3:
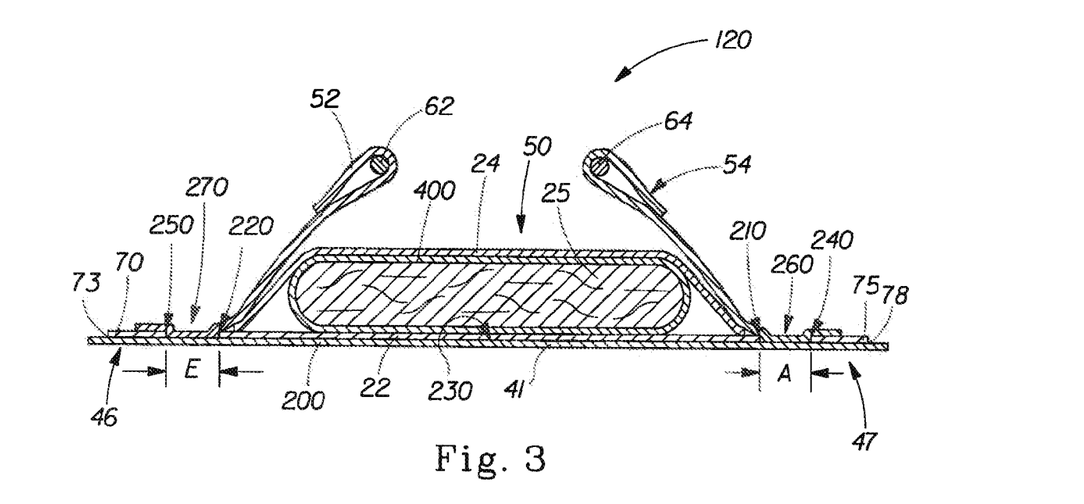
FIG. 3 is a cross-sectional view of one embodiment of the pant-type garment of FIG. 2 taken along the sectional line 3-3.

FIG. 1 shows one embodiment of a disposable pull-on garment of the present invention, namely a unitary disposable pull-on article 120. The disposable article 120 contains two leg openings 34 and a waist opening 36. The disposable article 120 comprises a chassis 41 having a front region 26; a back region 28; a crotch region 30 between the front region 26 and the back region 28; a wearer-facing surface 230 (FIG. 3) and a pair of opposing side regions 46 and 47. The absorbent assembly 50 is joined to the chassis 41 via the wearer-facing surface 230 (FIG. 3). The chassis, absorbent assembly, and various components thereof are explained in more detail herein.

As shown in FIG. 1 the chassis 41 comprises an outer cover 200. In one optional embodiment the outer cover 200 preferably has a relatively high elongation at breaking, and is more preferably stretchable or elongatable, yet more preferably drawable (but not necessarily elastomeric), without undue (and preferably without any), tearing or ripping. Illustrative outer cover 200 material includes, but is not limited to, nonwoven materials comprising: natural fibers, such as wood pulp fibers, cotton, rayon (also known as viscose) and combinations thereof; synthetic fibers, such as polyolefins, polyesters, and combinations thereof; and combinations thereof. The outer cover 200 may be formed in any conventional fashion, such as but not limited to, hydroentangling, carded, meltblown, airlaid and the like, and combinations thereof. In one optional embodiment, the outer cover is a carded nonwoven material, for example, obtainable from Havix Co., LTD., Gifu, Japan as E-2341. The outer cover is made of bi-component fibers of a polyethylene (PE) and a polypropylene (PP). The ratio of PE/PP is about 50/50. Another suitable carded nonwoven web having a ratio of PE/PP of about 50/50 is obtainable from Chisso Corp., Moriyama, Japan.

In another embodiment, the outer cover 200 is a spunbonded nonwoven material, for example, obtainable from Mitsui Petrochemical Industries, Ltd., Tokyo, Japan. The chassis is made of bi-component fibers of a polyethylene (PE) and a polypropylene (PP). The ratio of PE/PP is about 80/20.

In one optional embodiment of the present invention a region, several regions or the entire the chassis 41, such as the outer cover 200, may be subjected to mechanical treatment, such as zone activation. The chassis, or a part thereof, such as the pair of opposing side regions 46 and 47 or portions thereof, may be mechanically treated, such as by SELFing, ring rolling, and the like.

In another optional embodiment of the present invention an area of the chassis 41, such as the outer cover 200 and/or the pair of opposing side regions 46 and 47, may form a laminate, more preferably a stretch laminate or the like, with the stretchable members 70 and 75. The region of the chassis 41 forming the laminate with the stretchable members 70 and 75 are typically areas of the chassis 41 which are in direct contact with the stretchable members 70 and 75, such as the pair of opposing side regions 46 and 47. It is preferred that when the chassis 41 forms a laminate with the stretchable members 70 and 75 the chassis 41 has a relatively high elongation at breaking, and is more preferably stretchable or elongatable, yet more preferably drawable (but not necessarily elastomeric), without undue (and preferably without any), tearing or ripping. Stretchable members 70 and 75, and stretch laminates and the like are discussed and explained in more detail herein.

The pair of opposing side regions 46 and 47 are extensions of the chassis 41. This unitary construction of the disposable article 120 has the appearance and feel of conventional undergarments not only to the users, but also caregivers and others. This perception of the disposable article 120 by parties other than the users can provide additional reinforcement to a child who is toilet training (e.g., "What a big boy/girl you're wearing underwear!") and comfort and security to an adult by concealing the fact they are wearing a disposable pant-like absorbent article. Furthermore, this unitary construction means that it is much easier to make a comfortable disposable article 120 since the pair of opposing side regions 46 and 47 may be readily, and economically cut to various sizes and shapes. The size and shape will depend upon many factors, including but not limited to, size of article, intended users, style of article, type of article, material of chassis and the like and combinations thereof.

Additionally, the opposing side regions 46 and 47 provide a more comfortable and contouring fit by initially conformably fitting the disposable article 120 to the wearer and sustaining this fit throughout the time of wear well past when the disposable article 120 has been loaded with exudates since the stretchable members 70 and 75 allow the pair of opposing side regions 46 and 47 of the disposable article 120 to expand and contract. While not wishing to be limited by theory it is believed that the stretchable members 70 and 75 allows the pair of opposing side regions 46 and 47 to maintain the disposable article 120 snugly against the wearer's body near the hips, stomach and back.

In one embodiment of the present invention stretchable members 70 and 75 may each be a discrete unitary body or alternatively stretchable members 70 and 75 may be contiguous, that is, separated into different regions in contact with each other as illustrated in FIG. 1. In FIG. 1, the stretchable members 70 and 75 each comprise a front region 71 and 76 and a corresponding back region 73 and 78 contacting each other at seams 32. The contiguous regions 71, 73, 76, and 78 may each comprise any material suitable for use as stretchable members 70 and 75, such as but not limited to, "plane elastomeric material", stretch laminates and the like, which are discussed and explained in more detail herein.

In the disposable article 120 of FIG. 1 the seams 32 are located at the approximate mid point of the pair of opposing side regions 46 and 47, however there is nothing in this present invention which limits the seams 32 to only this location. Furthermore, the seams 32 may optionally include added features, such as but not limited to, tabs to aid in the removal of the garment. In an alternative embodiment, not shown in the figures, the seams 32 may include a resealable fastener, such as but not limited to, hook and loop fasteners, buttons, zippers, tab and slot, adhesives, co-adhesives and the like.

The absorbent assembly 50 is joined to the chassis 41 at the wearer-facing surface 230 (FIG. 3), such that, the absorbent assembly's pair of longitudinally oriented side edges 210 and 220 are in a spaced apart relationship with each of the stretchable member's pair of longitudinally oriented side edges 240 and 300, and 250 and 310, each defining a pair of longitudinally orientated non-elasticized portions 260 and 320, and 270 and 330 therebetween. It is preferred that the non-elasticized portions 260, 270, 320, and 330 have a relatively high elongation at breaking, and are more preferably stretchable or elongatable, yet more preferably drawable (but not necessarily elastomeric), without undue (and preferably without any), tearing or ripping.

Figure 2:
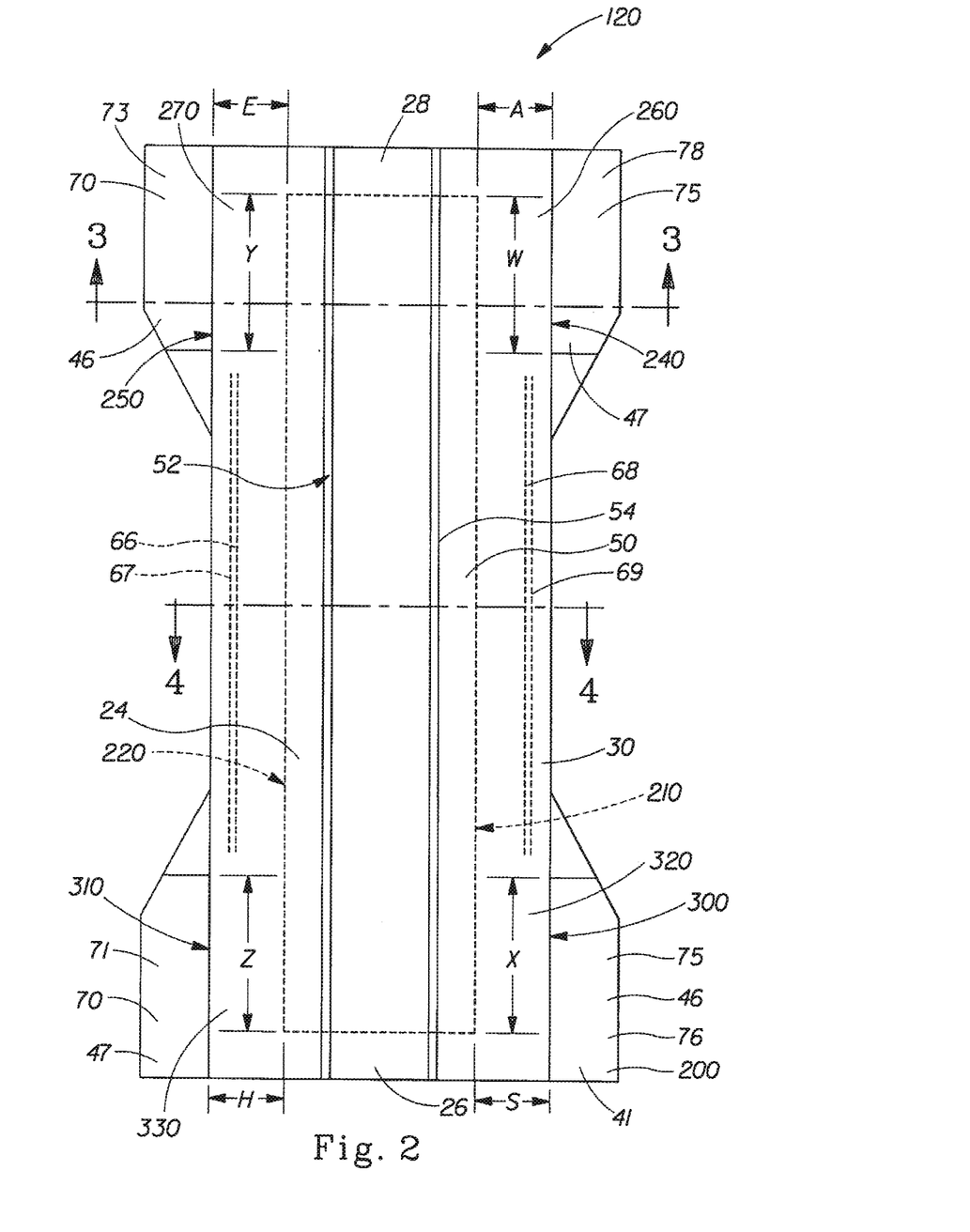
FIG. 2 is a simplified plan view of the pant-type garment of FIG. 1 in its flat, unseamed and uncontracted condition showing the various regions of the garment.

The longitudinally orientated non-elasticized portions 260, 270, 320, and 330 may be any suitable nonzero width A, S, E and H (FIGS. 2 and 3) and length W, X, Y and Z (FIG. 2). The longitudinally orientated non-elasticized portions 260, 270, 320, and 330 may be the same approximate width, that is, A E, S and H are all approximately equal, length, that is W X, Y and Z are all approximately equal, or they may be different. It is preferred that the longitudinally orientated non-elasticized portions 260, 270, 320, and 330 be the same approximate width, length and consequently the same approximate area. In one optional embodiment of the present invention the longitudinally orientated non-elasticized portions 260, 270, 320, and 330 are approximately the same width and are preferably from about 0.5 mm to about 26 mm, more preferably 0.5 mm to about 20 mm, even more preferably from about 1 mm to about 15 mm. In one optional embodiment of the present invention the longitudinally orientated non-elasticized portions 260, 270, 320, and 330 are approximately the same length and are preferably from about 75 mm to about 200 mm, more preferably 85 mm to about 175 mm, even more preferably from about 85 mm to about 150 mm.

The dimensions of the longitudinally orientated non-elasticized portions 260, 270, 320, and 330, such as width and length, depend upon many factors, including but not limited to: chassis dimensions; shape of the chassis; nonwoven material comprising the outer cover; the intended wearer of the pant-like absorbent article, for example, whether the article is a diaper or an adult incontinence product; the dimensions and/or shape of the absorbent assembly; the materials of the absorbent assembly; the size and/or shape of the stretchable members; the material comprising the stretchable members; the size and/or shape of the barrier cuff; the material comprising the barrier cuff; where and/or how the barrier cuffs are attached to the absorbent assembly; the outer cover and/or the stretchable members; and the like.

In one embodiment of the present invention the dimensions of the longitudinally orientated non-elasticized portions 260, 270, 320, and 330, may be used to determine the combined area of the front and longitudinally orientated non-elasticized portions of each of the opposing side regions 46 and 47. Its is preferred that this combined area of the front and rear longitudinally orientated non-elasticized portions of each of the opposing side regions 46 and 47 be from about 0.5% to about 25%, more preferably from about 0.5% to about 15% of the total surface area of the corresponding stretchable member 70 and 75. In this optional embodiment of the present invention it is preferred that the area of the front and rear longitudinally orientated non-elasticized portions 260 and 320 have a combined area from about 0.5% to about 25%, of the total surface area of stretchable member 75. Likewise, in this optional embodiment of the present invention it is preferred that the area of the front and rear longitudinally orientated non-elasticized portions 270 and 330 have a combined area from about 0.5% to about 25%, of the total surface area of stretchable member 70.

The inclusion of the longitudinally orientated non-elasticized portions 260, 270, 320, and 330 in a disposable article 120 offers many advantages over previous disposable pant-type garments, such as pull-on diapers. For example, the inclusion of the longitudinally orientated non-elasticized portions 260, 270, 320, and 330 when the stretchable members 70 and 75 comprise high quality elastomeric materials means a cost savings. This savings in elastomeric materials translates to a significant cost savings for disposable pull-on garments, which are produced in the hundreds of thousands, if not more, daily. That is, the amount of stretchable members 70 and 75 used is minimized, while the disposable article 120 still provides comparable, if not superior, fit and stretch to prior disposable pant-type garments. The barrier cuffs and the outer cover also provide stability and maintain the integrity of the disposable article 120.

FIG. 2 is a plan view of the disposable article 120 of FIG. 1 in its uncontracted state (except in the pair of opposing side regions 46 and 47 which are left in their relaxed condition) with the topsheet 24 facing the viewer, prior to the pair of opposing side regions 46 and 47 being joined together by the seams 32 as shown in FIG. 1.

The disposable article 120 includes an absorbent assembly 50 joined to the chassis 41 at wearer-facing surface 230 (FIG. 3). The absorbent assembly 50 comprises a liquid pervious topsheet 24, a liquid impervious backsheet 22 associated with the topsheet 24, and the absorbent core 25 positioned between the topsheet 24 and the backsheet 22, and a pair of longitudinally oriented side edges 210 and 220. The absorbent core 25 is shown surrounded by an optional core wrap 400. The topsheet 24 and the backsheet 22 may have length and width dimensions generally larger than those of the absorbent core 25.

The absorbent assembly 50 is joined to the chassis 41 at the wearer-facing surface 230 (FIG. 3), such that, the absorbent assembly's pair of longitudinally oriented side edges 210 and 220 are in a spaced apart relationship with each of the stretchable member's pair of longitudinally oriented side edges 240, 250, 300 and 310 defining a front and rear longitudinally orientated non-elasticized portions 260, 270, 320, and 330 therebetween. Preferably, the absorbent assembly 50 is permanently affixed, joined or attached to the chassis 41, for example via the outer-facing surface of the backsheet 22. The absorbent assembly 50 may be joined to the chassis 41 by any suitable attachment means known in the art. For example, the chassis 41 may be secured to the backsheet 22 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H.B. Fuller Japan Co., Ltd., Osaka, Japan as JM-6064.

The topsheet 24 is preferably compliant, soft to the touch, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant.

In one embodiment, the topsheet 24 is a nonwoven web that can provide reduced tendency for surface wetness; and consequently facilitate maintaining urine absorbed by the core 25 away from the user's skin, after wetting. One suitable topsheet material is a thermobonded carded web which is available as Code No. P-8 from Fiberweb North America, Inc. (Simpsonville, S.C., U.S.A.). Another suitable topsheet material is available as Code No. S-2355 from Havix Co., Japan. Yet another suitable topsheet material is a thermobonded carded web which is available as Code No. Profleece Style 040018007 from Amoco Fabrics, Inc. (Gronau, Germany).

In another embodiment topsheet 24 includes an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr, et al. on Jul. 31, 1984; and U.S. Pat. No. 5,006,394 "Multilayer Polymeric Film" issued to Baird on Apr. 9, 1991.

The absorbent core 25 can be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; melt-blown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the disposable article 120.

The absorbent core may include other optional components. One such optional component is the core wrap 400, i.e. a material, typically but not always a nonwoven material, which either partially or totally surrounds the core. Suitable core wrap materials include, but are not limited to, cellulose, hydrophilically modified nonwoven materials, perforated films and combinations thereof.

In one optional embodiment of the present invention the backsheet 22 comprises a liquid impervious film. The backsheet 22 is impervious to liquids (e.g., urine) and is preferably manufactured from a thin plastic film. However, more preferably the backsheet 22 permits vapors to escape from the disposable article 120. In a preferred embodiment, a microporous polyethylene film is used for the backsheet 22. A suitable microporous polyethylene film is manufactured by Mitsui Toatsu Chemicals, Inc., Nagoya, Japan and marketed in the trade as PG-P.

One suitable material for the backsheet 22 is a liquid impervious thermoplastic film having a thickness of from about 0.012 mm (0.5 mil) to about 0.051 mm (2.0 mils), preferably including polyethylene or polypropylene. Preferably, the backsheet 22 has a basis weight of from about 5 $g/m^2$ to about 35 $g/m^2$. However, it should be noted that other flexible liquid impervious materials may be used as the backsheet 22. Herein, "flexible" refers to materials which are compliant and which will readily conform to the general shape and contours of the wearer's body.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Illustrative, but nonlimiting adhesives, include adhesives manufactured by H.B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The disposable article 120 may also include one or more graphics. Graphics may be present on the outer cover 200, the backsheet 22, topsheet 24 and combinations thereof. These graphics may be present on either or both sides of the outer cover 200, the backsheet 22, topsheet 24 and the like. The graphics may be added to the disposable article 120 in any conventional fashion, such as but not limited to, ink jet printing, screen printing, photolithography and the like. These graphics may be of any suitable size and shape and would typically include graphics which would appear on underwear. The graphics may also be used to make the disposable article 120 appear more like underwear, such as a simulated "fly opening" for an disposable article 120 designed for boys.

The graphics may comprise one or more wetness indicator graphics, that is, the graphics appear, disappear, change shape and/or color, typically within about five minutes of when contacted by a bodily emission, such as urine, blood, feces and the like. In one optional embodiment of the present invention the disposable article 120 contains one or more wetness indicator graphics as well as one or more conventional graphics, that is, nonwetness indicating graphics.

The disposable article 120 may also include such other features (not shown) as are known in the art including, but not limited to, re-closable fastening system, lotion, acquisition layers, distribution layers, wetness indicators, sensors, elasticized waist bands and other similar additional elastic elements and the like, belts and the like, waist cap features, containment and aesthetic characteristics and combinations thereof. Additional illustrative, but non-limiting, information on construction, assembly, treatment and the various components of disposable diapers may be found in U.S. Pat. No. 3,860,003 to Buell; U.S. Pat. No. 5,151,092 to Buell; U.S. Pat. No. 5,221,274 to Buell; U.S. Pat. No. 5,554,145 to Roe et al. on Sep. 10, 1996; U.S. Pat. No. 5,569,234 to Buell et al.; U.S. Pat. No. 5,580,411 to Nease et al.; U.S. Pat. No. 6,004,306 to Robles et al.; U.S. Pat. No. 5,938,648 to LaVon et al.; U.S. Pat. No. 5,865,823 to Curro; U.S. Pat. No. 5,571,096 to Dobrin et al.; U.S. Pat. No. 5,518,801 to Chappell, et al.; U.S. Pat. No. 4,573,986 to Minetola et al.; U.S. Pat. No. 3,929,135, to Thompson; U.S. Pat. No. 4,463,045 to Ahr, et al.; U.S. Pat. No. 4,609,518 to Curro et al.; U.S. Pat. No. 4,629,643 to Curro et al.; U.S. Pat. No. 5,037,416 to Allen et al.; U.S. Pat. No. 5,269,775 to Freeland et al.; U.S. Pat. No. 4,610,678 to Weisman et al.; U.S. Pat. No. 4,673,402 to Weisman et al.; U.S. Pat. No. 4,888,231 to Angstadt; U.S. Pat. No. 5,342,338 to Roe; U.S. Pat. No. 5,260,345 to DesMarais et al.; U.S. Pat. No. 5,026,364 to Robertson; U.S. Pat. No. 3,848,594 to Buell; U.S. Pat. No. 4,846,815 to Scripps; U.S. Pat. No. 4,946,527 to Battrell; U.S. Pat. No. 4,963,140 to Robertson et al.; U.S. Pat. No. 4,699,622 to Toussant et al.; U.S. Pat. No. 5,591,152 to Buell et al.; U.S. Pat. No. 4,938,753 to Van Gompel, et al.; U.S. Pat. No. 5,669,897 to LaVon, et al.; U.S. Pat. No. 4,808,178 to Aziz et al.; U.S. Pat. No. 4,909,803 to Aziz et al.; U.S. Pat. No. 4,695,278 to Lawson; U.S. Pat. No. 4,795,454 issued to Dragoo; U.S. Pat. No. 5,607,760 to Roe on; U.S. Pat. No. 5,609,587 to Roe; U.S. Pat. No. 5,635,191 to Roe et al.; U.S. Pat. No. 5,643,588 to Roe et al.; U.S. Pat. No. 5,968,025 to Roe et al; U.S. Pat. No. 4,515,595 issued to Kievit et al; U.S. Pat. No. 5,330,458 issued to Buell et al; U.S. Pat. No. 2,075,189 issued to Galligan; U.S. Pat. No. 3,025,199 issued to Harwood; U.S. Pat. Nos. 4,107,364 and 4,209,563 issued to Sisson; U.S. Pat. No. 4,834,741 issued to Sabee; U.S. Pat. No. 5,190,563, issued to Herron; U.S. Pat. No. 5,234,423, issued to Young, et al; U.S. Pat. No. 5,147,345, issued to Young, et al; U.S. Pat. No. 6,443,940, issued to Ashton et al; U.S. Pat. No. 4,834,735, issued to Alemany et al; U.S. Pat. No. 4,988,344 issued to Reising, et al; U.S. Pat. No. 4,988,345 issued to Reising; and EP 0797968A1 (Kurt et al.) published on Oct. 1, 1997;

FIG. 3 is a cross-sectional view of a one embodiment of the present invention taken along the section line 3-3 of FIG. 2 in the direction of the arrows, i.e. towards the back region 28 of the disposable article 120. FIG. 3 illustrates the back portion of each of the pair of opposing side regions 46 and 47 each extending laterally outward from the chassis 41, and two opposing barrier cuffs 52 and 54, each containing one or more elastic strands 62, and 64. Although FIG. 3 depicts only the structure of the back of the side panels 46 and 47 and the chassis 41 in the back region 28, preferably a similar structure is also provided in the front region 26.

The unitary disposable pant-like absorbent articles of the present invention comprise at least one barrier leg cuff, preferably at least two barrier leg cuffs 52 and 54 attached to the chassis 41 and absorbent assembly 50 via the pair of longitudinally oriented side edges 210 and 220 as illustrated in FIG. 3. (The leg cuffs can be and are sometimes also referred to as leg bands, side flaps, leg cuffs, barrier cuff, elastic cuffs or gasketing cuffs.) The barrier leg cuffs provide improved containment of liquids and other body exudates. The barrier leg cuffs may include several different embodiments for reducing the leakage of body exudates in the leg regions. Illustrative examples of suitable barrier leg cuffs may be found in U.S. Pat. No. 3,860,003 entitled "Contractable Side Portions for Disposable Diaper" issued to Buell on Jan. 14, 1975; U.S. Pat. No. 4,909,803 entitled "Disposable Absorbent Article Having Elasticized Flaps" issued to Aziz et al. on Mar. 20, 1990; U.S. Pat. No. 4,695,278 entitled "Absorbent Article Having Dual Cuffs" issued to Lawson on Sep. 22, 1987; U.S. Pat. No. 4,795,454 entitled "Absorbent Article Having Leakage-Resistant Dual Cuffs" issued to Dragoo on Jan. 3, 1989; and U.S. Pat. No. 4,704,115 entitled "Disposable Waist Containment Garment" issued to Buell on Nov. 3, 1987.

While each barrier leg cuff 52 and 54 may be configured to be similar to any of the leg bands, side flaps, barrier cuffs, or elastic cuffs described herein, it is preferred that each barrier leg cuff 52 and 54 includes one or more elastic strands 62, and 64.

The barrier leg cuffs may comprise any suitable material. Illustrative suitable material, include but are not limited to, polyesters, rayon, cellulose, polyethylene, polypropylene, and combinations thereof. In one optional embodiment of the present invention the barrier leg cuff is liquid impermeable.

In FIG. 3 the absorbent assembly 50 has a pair of longitudinally oriented side edges 210 and 220. The pair of longitudinally oriented side edges 210 and 220 are the outermost longitudinal side edges of the absorbent assembly 50, i.e., in the embodiment illustrated in FIG. 3 the pair of longitudinally oriented side edges of the backsheet 22. However, the pair of longitudinally oriented side edges 210 and 220 are not limited to the longitudinally oriented side edges of the backsheet 22, and may be any pair of longitudinally oriented side edges which form the outer longitudinally oriented side edges of the absorbent assembly, such as but not limited to the pair of longitudinal side edges of the topsheet.

FIG. 3 illustrates an optional embodiment of the present invention where the barrier leg cuffs 52 and 54 are attached to the stretchable members 70 and 75 and the chassis 41 in an overlapping manner. The opposing barrier cuffs 52 and 54 are also attached to the absorbent assembly via the back sheet 22 and the top sheet 24. This attachment arrangement of overlapping the opposing barrier cuffs 52 and 54 over the stretchable members 70 and 75 and the chassis 41 not only provides additional strength and support but also assists in making the pull-on garment more garment like in appearance. The barrier leg cuffs 52 and 54 may be attached in any suitable fashion, including but not limited to, adhesive, heat bonds, pressure bonds, ultrasonic bonds, dynamic mechanical bonds, or any other suitable attachment means or combinations of these attachment means as are known in the art.

Figure 4:
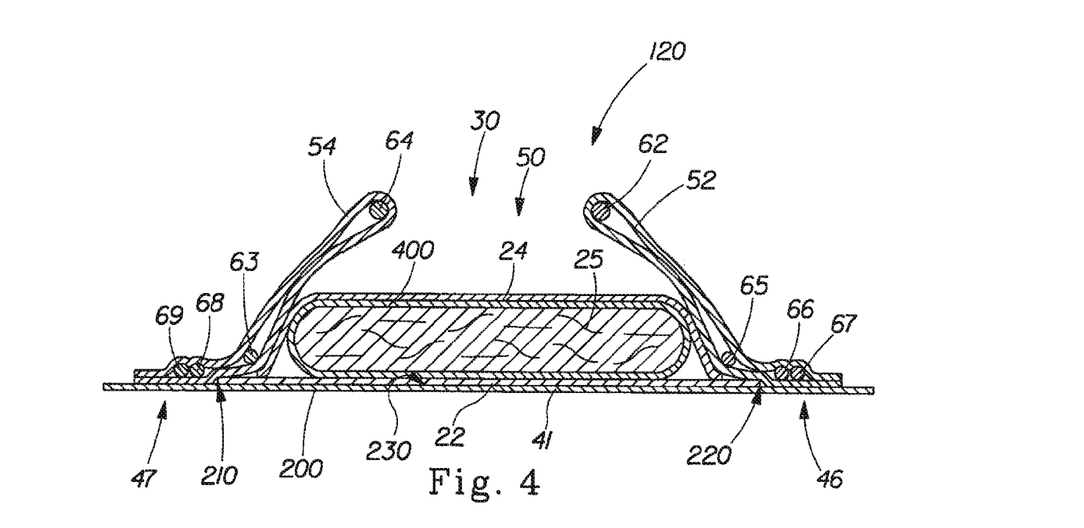
FIG. 4 is a cross-sectional view of one embodiment of the pant-type garment of FIG. 2 taken along the sectional line 4-4.

FIG. 4 is a cross-sectional view of a one optional embodiment of the present invention taken along the section line 4-4 of FIG. 2 in the direction of arrows 4, i.e., in the crotch region 24 of the disposable article 120 looking towards the front 26 of the disposable article 120. (The opposite direction of FIG. 3) FIG. 4 illustrates an optional embodiment of the present invention where the barrier leg cuffs 52 and 54 include additional elastic strands, also know as leg elastic 63, 65, 66, 67, 68 and 69. As illustrated in the embodiment of FIG. 2, the additional elastic strands 63, 65, 66, 67, 68 and 69 are not present in any of the longitudinally orientated non-elasticized portions 260 and 320, and 270 and 330 therebetween. These elastic strands may be any suitable elastic material as described herein.

The stretchable members 70 and 75 may comprise any suitable stretchable material, such as but not limited to, elastic strands, elastic sheets, films, elastic scrim, elastic, and the like, and combinations thereof. The stretchable members 70 and 75 are preferably joined to, more preferably directly secured to, the respective pair of opposing side regions 46 and 47 of the chassis 41 through an adhesive. Preferably, the adhesive is applied in a spiral glue pattern. In one optional embodiment, the adhesive is a flexible adhesive with an amorphous and crystallizing component. Such a preferred adhesive is made by Nitta Findley Co., Ltd., Osaka, Japan, under the designation H2085F. Alternatively, the stretchable members 70 and 75 may be joined to the respective pair of opposing side regions 46 and 47 of the chassis 41 by any other bonding means known in the art which include heat bonds, pressure bonds, ultrasonic bonds, dynamic mechanical bonds, or combinations of these attachment means.

Preferably, the elastomeric members 70 and 75 are stretchable in at least one direction, preferably in the lateral direction to generate a retention (or sustained) force that is optimal to prevent the disposable article 120 from drooping, sagging, or sliding down from its position on the torso without causing the red marking on the skin of the wearer.

The stretchable members 70 and 75 are respectively operatively joined to one of the pair of opposing side regions 46 and 47 of the chassis 41 to allow the stretchable members 70 and 75 to be elastically stretchable in at least the lateral direction. In a preferred embodiment, the stretchable members 70 and 75 are operatively joined to the opposing side regions 46 and 47 of the chassis 41 by securing them to opposing side regions 46 and 47 of the chassis 41 while in a substantially untensioned (zero strain) condition.

The stretchable members 70 and 75 may optionally be operatively joined to the opposing side regions 46 and 47 of the chassis 41 by using either an intermittent bonding configuration or a substantially continuous bonding configuration, thereby forming a stretch laminate. Herein, "intermittently" bonded means the stretchable member and the side region to which it is attached are initially bonded to one another at discrete spaced apart points or the stretchable member and the side region to which it is attached are substantially unbonded to one another at discrete spaced apart areas. Conversely, a "substantially continuously" means the stretchable member and the side region to which it is attached are initially bonded substantially continuously to one another throughout the areas of interface. It is preferred that the stretchable member be bonded over all or a significant portion of the stretchable member so that the side region to which it is attached can elongate or draw without causing rupture, and the layers of the stretch laminates are preferably bonded in a configuration that maintains all of the layers of the stretch laminate in relatively close adherence to one another after the incremental mechanical stretching operation. The layers of the stretch laminate may be bonded, more preferably substantially continuously bonded, together using an adhesive. In a one optional embodiment, the adhesive selected is applied with a control coat spray pattern at a basis weight of about 7.0 grams/square m. The adhesive pattern width is about 6.0 cm. The adhesive is preferably an adhesive such as is available from Nitta Findley Co., Ltd., Osaka, Japan, under the designation H2085F. Alternatively, the stretchable member and any other components of the stretch laminates may be intermittently or continuously bonded to one another using heat bonding, pressure bonding, ultrasonic bonding, dynamic mechanical bonding, or any other method as is known in the art.

After the stretchable members 70 and 75 are operatively joined to opposing side regions 46 and 47 of the chassis 41, it is preferred that at least a portion of the resultant composite stretch laminate is then subjected to mechanical stretching sufficient to permanently elongate the non-elastic components which are, for example, opposing side regions 46 and 47. The composite stretch laminate is then allowed to return to its substantially untensioned condition. The pair of opposing side regions 46 and 47 of the chassis 41 is thus formed into "zero strain" stretch laminates. (Alternatively, the stretchable members 70 and 75 could be operatively joined in a tensioned condition and then subjected to mechanical stretching; although this is not as preferred as a "zero strain" stretch laminate.) Herein, "zero strain" stretch laminate refers to a laminate included of at least two plies of material which are secured to one another along at least a portion of their coextensive surfaces while in a substantially untensioned ("zero strain") condition; one of the plies including a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically stretchable, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992.

In an alternative embodiment of the present invention the stretchable members 70 and 75 may be subjected to mechanical stretching and then operatively joined to opposing side regions 46 and 47 of the chassis 41. The laminate is then allowed to return to its substantially untensioned condition, thereby gathering the opposing side regions 46 and 47 of the chassis 41 and forming a stretch bonded laminates. Herein, "stretch bonded" laminates refers to a laminate of at least two plies of material which are secured to one another along at least a portion of their coextensive surfaces while in an elastomeric layer thereof is a substantially tensioned condition. Typically, one of the plies is a material which is stretchable and elastomeric (i.e., will return substantially to its untensioned dimensions after an applied tensile force has been released). The second ply which is gatherable so that upon stretching the second ply will be, at least to a degree, able to return to its original ungathered configuration. The resulting stretch bonded laminate is thereby rendered elastically stretchable, at least up to the point of ungathered configuration. It is also within the scope of the present invention to use combinations of stretch bonded laminates and "zero strain" stretch laminates" (described herein).

Figure 5:
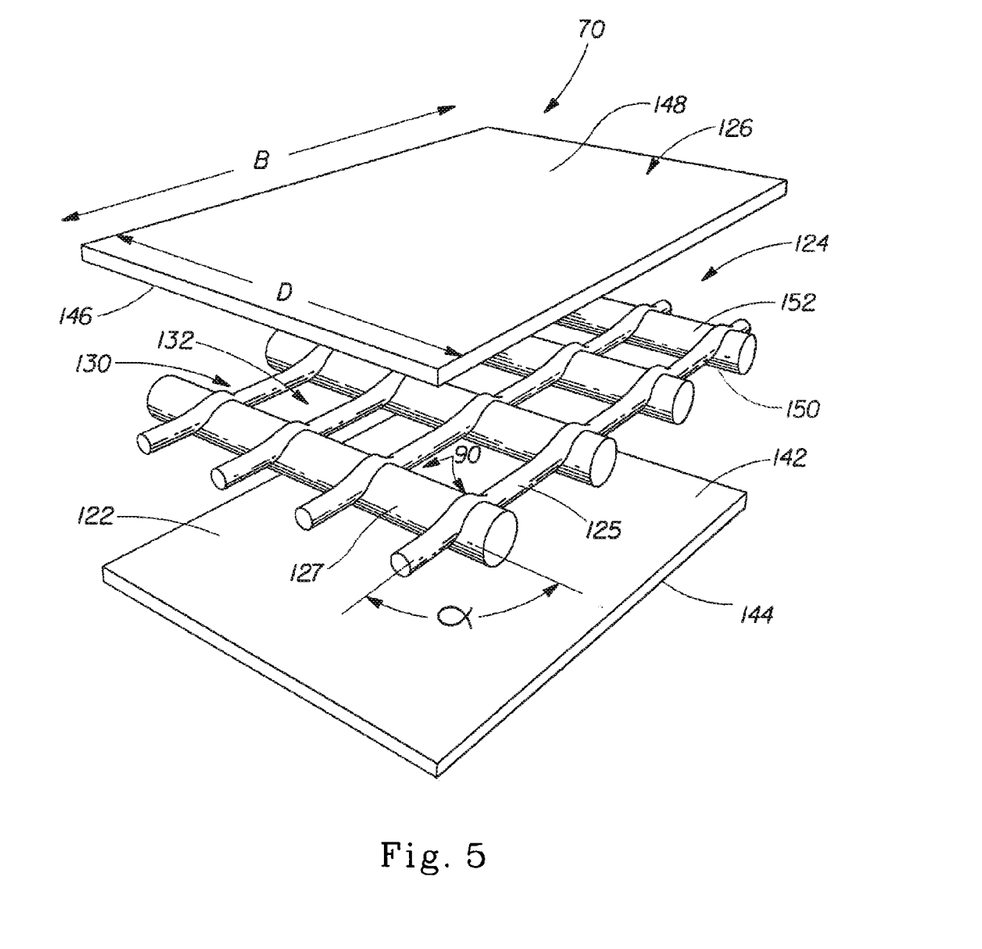
FIG. 5 is an exploded view of a stretchable member 70 of one optional embodiment.

FIG. 5 illustrates an exploded view of one possible embodiment of the stretchable member 70 and includes a plane elastomeric material 124. It is to be understood that while stretchable member 75 is not illustrated in FIG. 4, it may be identical or substantially similar. Herein, "plane elastomeric material" refers to elastomeric materials which continuously extend in two dimensional directions. Preferred plane elastomeric materials include a scrim, a perforated (or apertures formed) film, an elastomeric woven or nonwoven, and the like. In a preferred embodiment, the plane elastomeric material 124 includes at least a portion that has a nonuniform lateral width.

Referring to FIG. 5, the stretchable member 70 includes the elastomeric material 124 having a first surface 150 and a second surface 152 opposing the first surface 150, and a first coverstock layer 122 which is joined to the first surface 150 of the elastomeric material 124. In a preferred embodiment, the first coverstock layer 122 is joined to the first surface 150 of the elastomeric material 124 by an adhesive. More preferably, the stretchable member 70 further includes a second coverstock layer 126 which is joined to the second surface 152 of the elastomeric material 124 by an adhesive.

In the preferred embodiment shown in FIG. 5, the elastomeric material 124 has a plurality of first strands 125 and a plurality of second strands 127. The plurality of first strands 125 intersect the plurality of second strands 127 at nodes 130 at a predetermined angle α (alpha), forming a net-like open structure having a plurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. Preferably, the first and second strands 125 and 127 are substantially straight and substantially parallel to one another. Preferably, the first strands 125 intersect the second strands 127 at nodes 130 such that the angle α is about 90 degrees. The first and second strands 125 and 127 are preferably joined or bonded at nodes 90.

In the embodiment shown in FIG. 5, the stretchable member 70 includes first and second coverstock layers 122 and 126, and elastomeric material 124 disposed in the first and second coverstock layers 122 and 126. The first coverstock layer 122 has an inner surface 142 and an outer surface 144. The inner surface 142 of the first coverstock layer 122 is the surface that is positioned facing the elastomeric material 124. The second coverstock layer 126 also has an inner surface 146 and an outer surface 148. The inner surface 146 of the second coverstock layer 126 is the surface that is positioned facing the elastomeric material 124. The elastomeric material 124 also has two planar surfaces, first surface 150 and second surface 152, each of which is substantially parallel with the planes of the first and second coverstock layers 122 and 126. The first surface 150 is that planar surface of the elastomeric material 124 that is most closely adjacent with the inner surface 142 of first coverstock layer 122. The second surface 152 is that planar surface of elastomeric material 124 that is most closely adjacent to the inner surface 146 of the second coverstock layer 126.

In optional embodiment of the present invention one of the coverstock layers, such as but not limited to the second coverstock layer 126, may be the outer cover layer 200. In this preferred embodiment of the present invention the stretchable member 70 would comprise an elastomeric material 124 and a first coverstock layer 122 attached to the elastomeric material's 124 surface facing the inner surface 142 of the first coverstock layer 122, typically the first surface 150. The elastomeric material's 124 second surface is attached to the outer cover layer 200.

When one of the coverstock layers, is the outer cover layer 200, the portion of the outer cover layer 200, to which the elastomeric material 124 is attached, or a close approximation thereof, may be subjected to any treatment or further processing, mechanical or otherwise, that may be done on the coverstock layers 122 and 126. It is preferred that if the coverstock layer is subjected to further treatment or processing the corresponding region of the outer cover 200 to which the elastomeric material 124 is attached be subjected to the same or similar treatment or processing.

Since the stretchable member 70 will be subjected to mechanical stretching before and during use, the first and second coverstock layers 122 and 126 preferably have a relatively high elongation at breaking, and are more preferably stretchable or elongatable, yet more preferably drawable (but not necessarily elastomeric), without undue (and preferably without any), tearing or ripping. Further, the first and second coverstock layers 122 and 126 are preferably compliant, soft to the touch, and non-irritating to the wearer's skin and give the article the feel and comfort of a cloth garment. Suitable materials for the first and second coverstock layers 122 and 126 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Preferably, each of the first and second coverstock layers 122 and 126 is an identical consolidated nonwoven material. An exemplary preferred nonwoven material is manufactured by the Fiberweb North America, Inc. (Simpsonville, S.C., U.S.A.) under the designation Sofspan 200. This material has a basis weight of 25 g/m² before consolidation and a basis weight of about 63 g/m² after consolidation. Herein, "basis weight" is the weight of one square meter of planar web material. Alternatively, highly strainable nonwoven materials may be used. Alternatively, the first and second coverstock layers 122 and 126 need not be of identical materials, as long as the desired performance requirements, such as elastic performance, softness, flexibility, breathability and durability, are met. Herein, "consolidated nonwoven material" means a nonwoven material that has been gathered or necked under mechanical tension in the structural direction D so that the material can elongate in the structural direction D under low force.

The elastomeric material 124 may be formed in a wide variety of sizes, forms and shapes. In a preferred embodiment, the elastomeric material 124 is in the form of a continuous plane layer. Preferred forms of continuous plane layer include a scrim, a perforated (or apertures formed) film, an elastomeric woven or nonwoven, and the like. The continuous plane layer may take any shape which can be suitably provided in the opposing side regions 46 and 47 of the chassis 41. Preferred shapes of continuous plane layer include a quadrilateral including a rectangle and a square, a trapezoid, and the other polygons.

Elastomeric materials which have been found to be especially suitable for the elastomeric material 124 are styrenic block copolymer based scrim materials, perforated (or apertured) elastic films, preferably with a thickness of from about 0.05 mm to about 1.0 mm (0.002 inch-0.039 inch). Other suitable elastomeric materials for the elastomeric material 124 include "live" synthetic or natural rubber, other synthetic or natural rubber foams, elastomeric films (including heat shrinkable elastomeric films), elastomeric woven or nonwoven webs, elastomeric composites, or the like.

Another suitable elastomeric material 124 is manufactured by the Conwed Plastics Company (Minneapolis, Minn., U.S.A.) under the designation X02514. This material has about 12 elastic strands per inch in the structural direction B (i.e., the first strands 125) and about 7 elastic strands per inch in the structural direction D (i.e., the second strands 127).

Figure 6:
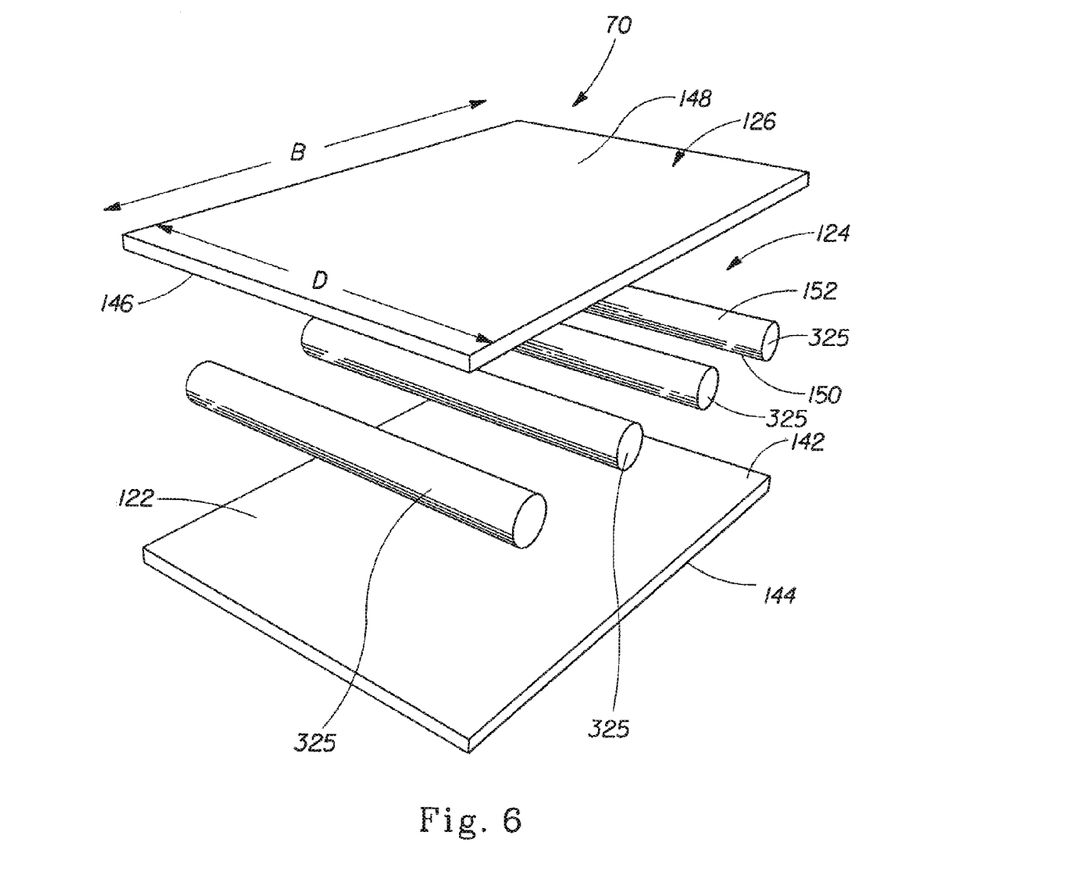
FIG. 6 is an exploded view of a stretchable member 70 of another optional embodiment.

In an alternative embodiment, the elastomeric material 124 is in the form of discrete strands (or strings), preferably parallel or non-overlapping strands, which are not connected to each other. An illustration of this alternative embodiment is illustrated in FIG. 6. The elastomeric material 124 has a plurality of strands 325. Other orientations of the plurality of strands 325, such as but not limited to a plurality of strands orientated in the direction B, are within the scope of the present invention.

Figure 7:
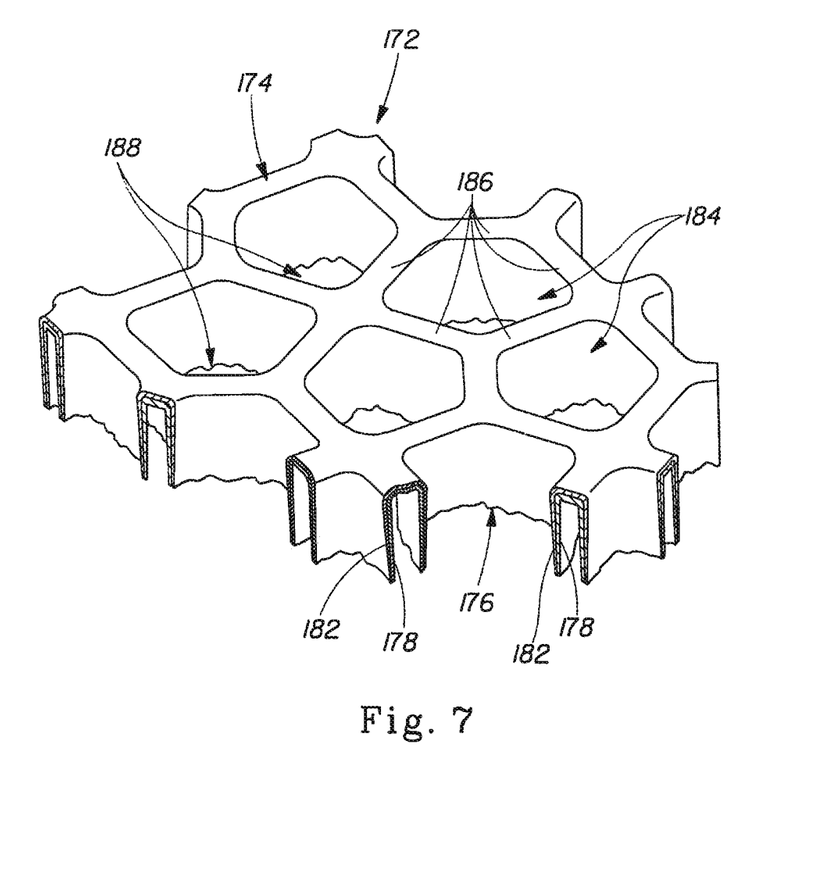
FIG. 7 is a fragmentary enlarged perspective illustration of an alternative embodiment of the elastomeric material 124.

In one optional embodiment, the elastomeric material 124 is a porous, macroscopically-expanded, three-dimensional elastomeric web 172 as shown in FIG. 7. The web 172 has a continuous first surface 174 and a discontinuous second surface 176 remote from first surface 174. The elastomeric web 172 preferably comprises a formed film having at least two polymeric layers, with at least one of the layers being an elastomer layer 178 and at least one of the other layers being a substantially less elastomeric skin layer 182. The elastomeric web exhibits a multiplicity of primary apertures 184 in the first surface 174 of the web 172, the primary apertures 184 being defined in the plane of the first surface 174 by a continuous network of interconnecting members 186. Each interconnecting member 186 exhibits an upwardly concave-shaped cross-section along its length. The interconnecting members 186 terminate substantially concurrently with one another to form a secondary aperture 188 in the plane of the second surface of the web. The primary apertures 184 may have any shape. The detail of such a structure and the method to manufacture is disclosed in U.S. patent application Ser. No. 08/816,106, filed Mar. 14, 1997. A preferred porous elastomeric material 124 is manufactured by the Tredegar Film Products under the designation X-25007.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A unitary disposable pant-like absorbent article for containing bodily wastes from a wearer, the article comprising:
an outer cover comprising a wearer-facing surface and an opposing garment facing surface, the outer cover defining a lateral width and a longitudinal length, and having a front waist region, a rear waist region, and a crotch region located longitudinally between the front waist region and the rear waist region, wherein the front waist region of the outer cover extends laterally outward in opposing directions to define first and second front side regions, wherein the rear waist region of the outer cover extends laterally outward in opposing directions to define first and second rear side regions, wherein the front and rear side regions extend laterally outward beyond a narrowest lateral width defined by the crotch region, and wherein the outer cover defines a pant-like garment having two leg openings and a waist opening when the first front and rear side regions are connected and when the second front and rear side regions are connected;
a first front stretchable member connected with and forming a laminate with the first front side region, the first front stretchable member having a first longitudinally oriented side edge and a second longitudinally oriented side edge laterally outboard of the first longitudinally oriented side edge, and wherein the first longitudinally oriented side edge is entirely disposed on the wearer-facing surface of the outer cover;
a second front stretchable member connected with and forming a laminate with the second front side region, the second front stretchable member having a first longitudinally oriented side edge and a second longitudinally oriented side edge laterally outboard of the first longitudinally oriented side edge, and wherein the first longitudinally oriented side edge is entirely disposed on the wearer-facing surface of the outer cover;
a first rear stretchable member connected with and forming a laminate with the first rear side region, the first rear stretchable member having a first longitudinally oriented side edge and a second longitudinally oriented side edge laterally outboard of the first longitudinally oriented side edge, and wherein the first longitudinally oriented side edge is entirely disposed on the wearer-facing surface of the outer cover;
a second rear stretchable member connected with and forming a laminate with the second rear side region, the second rear stretchable member having a first longitudinally oriented side edge and a second longitudinally oriented side edge laterally outboard of the first longitudinally oriented side edge, and wherein the first longitudinally oriented side edge is entirely disposed on the wearer-facing surface of the outer cover;
an absorbent assembly comprising a liquid pervious topsheet, a liquid impervious backsheet associated with the topsheet and an absorbent core disposed between the topsheet and the backsheet, the absorbent assembly being joined to the wearer-facing surface of the outer cover and being fully laterally inboard of the first and second, front and rear side regions, the absorbent assembly having a first longitudinally oriented side edge laterally opposed from a second longitudinally oriented side edge;
wherein the first longitudinally oriented side edge of the absorbent assembly is spaced laterally inboard from the first longitudinally oriented side edge of the first front stretchable member to define a first front longitudinally orientated non-elasticized gap region of the outer cover laterally extending between the first longitudinally oriented side edge of the absorbent assembly and the first longitudinally oriented side edge of first front stretchable member;
wherein the first longitudinally oriented side edge of the absorbent assembly is spaced laterally inboard from the first longitudinally oriented side edge of the first rear stretchable member to define a first rear longitudinally orientated non-elasticized gap region of the outer cover laterally extending between the first longitudinally oriented side edge of the absorbent assembly and the first longitudinally oriented side edge of first rear stretchable member;
wherein the second longitudinally oriented side edge of the absorbent assembly is spaced laterally inboard from the first longitudinally oriented side edge of the second front stretchable member to define a second front longitudinally orientated non-elasticized gap region of the outer cover laterally extending between the second longitudinally oriented side edge of the absorbent assembly and the first longitudinally oriented side edge of second front stretchable member;
wherein the second longitudinally oriented side edge of the absorbent assembly is spaced laterally inboard from the first longitudinally oriented side edge of the second rear stretchable member to define a second rear longitudinally orientated non-elasticized gap region of the outer cover laterally extending between the second longitudinally oriented side edge of the absorbent assembly and the first longitudinally oriented side edge of second rear stretchable member; and
a barrier cuff connected with one of the longitudinally oriented side edges of the absorbent assembly.

2. The unitary pant-like disposable absorbent article of claim 1, wherein the barrier cuff is also attached to one of the stretchable members, thereby overlapping one of the corresponding longitudinally orientated non-elasticized gap regions.

3. The unitary pant-like disposable absorbent article of claim 1, wherein each of the front longitudinally orientated non-elasticized regions and the rear longitudinally orientated non-elasticized gap regions independently have a width of from about 0.5 mm to about 26 mm.

4. The unitary pant-like disposable absorbent article of claim 1, wherein the front longitudinally orientated non-elasticized gap regions and the rear longitudinally orientated non-elasticized gap regions have a combined area from about 0.5% to about 25%, of the total surface area of the corresponding stretchable member.

5. The unitary pant-like disposable absorbent article of claim 4, wherein the front longitudinally orientated non-elasticized gap regions and the rear longitudinally orientated non-elasticized gap regions have a combined area from about 0.5% to about 15%, of the total surface area of the corresponding stretchable member.

6. The unitary pant-like disposable absorbent article of claim 1, wherein the barrier cuff is liquid impermeable.

7. The unitary pant-like disposable absorbent article of claim 1, wherein the outer cover is selected from the group consisting of polyethylene, polypropylene, polyester, cellulose, rayon and combinations thereof.

8. The unitary pant-like disposable absorbent article of claim 1, wherein the barrier cuff is also attached to the topsheet.

9. The unitary pant-like disposable absorbent article of claim 1, further comprising a second barrier cuff.

10. The unitary pant-like disposable absorbent article of claim 1, wherein at least one of the stretchable members comprises a "zero strain" stretch laminate.

11. The unitary pant-like disposable absorbent article of claim 10, wherein the "zero strain" stretch laminate comprises a porous, macroscopically-expanded, three-dimensional elastomeric web.

* * * * *